US012788882B2

(12) United States Patent
Contreras et al.

(10) Patent No.: US 12,788,882 B2
(45) Date of Patent: Nov. 10, 2026

(54) INFUSION PUMP HAVING NEXT ACTION INDICATOR TAB

(71) Applicant: B. Braun Medical Inc., Bethlehem, PA (US)

(72) Inventors: William Contreras, Nutley, NJ (US); Benjamin Loomis, Topton, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 938 days.

(21) Appl. No.: 18/106,230

(22) Filed: Feb. 6, 2023

(65) Prior Publication Data

US 2024/0261500 A1 Aug. 8, 2024

(51) Int. Cl.

*G06F 3/048* (2013.01)
*A61M 5/142* (2006.01)
*A61M 5/172* (2006.01)

(52) U.S. Cl.

CPC ............ *A61M 5/172* (2013.01); *A61M 5/142* (2013.01); *A61M 2205/502* (2013.01); *A61M 2205/52* (2013.01)

(58) Field of Classification Search

CPC .................. A61M 5/172; A61M 5/142; A61M 2205/502; A61M 2205/52

See application file for complete search history.

(56) References Cited

U.S. PATENT DOCUMENTS 7,020,844 B2 3/2006 Trevino et al.
7,881,946 B1 2/2011 Yehuda et al.
7,945,452 B2 5/2011 Fathallah et al.
8,250,483 B2 8/2012 Blomquist
8,298,167 B2 10/2012 Peters et al.
8,856,668 B2 10/2014 Niesslein et al.
(Continued)

FOREIGN PATENT DOCUMENTS

WO 2017062549 A1 4/2017

OTHER PUBLICATIONS

International Search Report and Written Opinion for International Application No. PCT/US2024/013289, dated May 17, 2024 (May 17, 2024)—14 pages.

(Continued)

*Primary Examiner* — David Phantana-angkool
(74) *Attorney, Agent, or Firm* — CM Law; Stephen J. Weed

(57) ABSTRACT

An infusion pump includes a multi-tabbed graphical user interface (GUI) that guides the user to the next tab to select during programming of the infusion pump. The GUI includes tabs that correspond to categories of parameters for entry (e.g., patient information, drug information, infusion information). As the data is entered, the operator selects the tabs (moving from left to right) and enters required parameters until all required parameters have been entered. Due to the number of items presented under a particular tab, it may not be readily apparent to the operator when the operator has entered all required parameters and can move on to the next tab. Accordingly, the GUI presents an indicator (e.g., small triangle) on or adjacent the next tab as soon as the required fields are completed, which guides the operator and speeds up programming when the required fields constitute less than the total number of fields.

20 Claims, 7 Drawing Sheets

(56) References Cited

U.S. PATENT DOCUMENTS

| | | | | |
|---|---|---|---|---|
| 9,240,002 | B2 * | 1/2016 | Hume | G06Q 10/10 |
| 9,662,438 | B2 * | 5/2017 | Kamen | A61M 5/14244 |
| 10,255,408 | B2 | 4/2019 | Blomquist | |
| 10,628,518 | B1 | 4/2020 | Francois | |
| 12,491,307 | B2 * | 12/2025 | Omar | A61M 1/72 |
| 2006/0229557 | A1 * | 10/2006 | Fathallah | G16H 40/63 705/2 |
| 2008/0033749 | A1 | 2/2008 | Blomquist | |
| 2010/0100037 | A1 * | 4/2010 | Cozmi | G16Z 99/00 128/920 |
| 2016/0283683 | A1 * | 9/2016 | Ferrarini | A61M 60/585 |
| 2018/0008787 | A1 * | 1/2018 | Schriver | A61M 5/365 |
| 2018/0304010 | A1 * | 10/2018 | DeBelser | A61M 5/14244 |
| 2019/0381232 | A1 | 12/2019 | Crnkovich et al. | |
| 2021/0020292 | A1 | 1/2021 | Zaccarelli et al. | |
| 2022/0362467 | A1 * | 11/2022 | Kamen | A61M 5/1723 |
| 2023/0166033 | A1 * | 6/2023 | Lee | G16H 20/17 604/151 |
| 2024/0033427 | A1 * | 2/2024 | Budiman | G16H 40/63 |
| 2024/0261500 | A1 * | 8/2024 | Contreras | G06F 3/0481 |
| 2024/0342362 | A1 * | 10/2024 | Burnard | A61M 5/14228 |

OTHER PUBLICATIONS

Medtronic: “SynchroMed II Infusion System. Programming Reference Guide”, Synchromed II Infusion System. Programming Reference Guide, Dec. 31, 2008 (Dec. 31, 2008), pp. 1-80, XP007915605.

Raluca Budiu: “Wizards: Definition and Design Recommendations”, Jul. 10, 2017 (Jul. 10, 2017), XP093160017.

* cited by examiner

INFUSION PUMP HAVING NEXT ACTION INDICATOR TAB

FIELD OF THE INVENTION

The present disclosure is related to infusion pumps and, more particularly, to infusion pumps having an indicator tab identifying a next action to be performed to program the infusion pump.

BACKGROUND

Infusion pumps deliver controlled doses of fluids such as medications, analgesics, and nutrition to patients. Infusion pumps are particularly well suited to delivering controlled doses of fluids over long periods of time, e.g., several hours or days. While many infusion pumps are designed for bedside use, there are ambulatory versions available. Ambulatory infusion pumps allow a patient to move around while the infusion pump is in use.

Syringe pumps and peristaltic pumps are two conventional types of infusion pumps. A syringe pump depresses a cylinder within a syringe to deliver fluid from the syringe to a patient. A peristaltic pump acts on a tube to control the rate of fluid flow through the tube from a bottle or bag of fluid to a patient. Precise delivery of fluids are desirable to optimize treatment of a patient as there are many fluids where small variations can be critical.

Infusion pumps are typically setup and programmed by medical professionals in a medical setting. However, ambulatory infusion pumps may be operated by a patient in a home setting. Clear guidance for safe programming and operation of infusion pumps by untrained users is useful to avoid operator error.

SUMMARY

Examples described herein are directed to methods and infusion pumps for delivering fluids to a patient. In sample configurations, the infusion pump includes a multi-tabbed graphical user interface (GUI) that guides the user to the next tab to select (e.g., by placing an indicator such as a small triangle, arrow, colored square, flashing circle, or other shape/pattern next to the tab) during programming of the infusion pump. The multi-tabbed GUI includes tabs that correspond to categories of parameters for entry (e.g., patient information, drug information, infusion information). The tabs are presented in order, with the first parameters to be entered accessed by selecting a tab on the far left. As the information is completed, the operator selects the tabs (moving from left to right) until all required parameters have been entered. The operator is required to fill in all required parameters of a particular category before moving on to the next category. However, due to the number of items present under a particular tab, it may not be readily apparent to the operator when the operator has entered all required parameters under a particular tab and can move on to the next tab.

Accordingly, the GUI is adapted to guide the operator in the selection of the next tab by presenting an indicator next to the next tab when all the required parameters under the current tab have been entered. In sample configurations, the GUI presents the indicator on or adjacent to the next tab as soon as the required fields are completed, even for those situations where the required fields needed to complete a step constitute less than the total number of fields. By presenting the indicator as soon as the required fields have been completed, even when other optional fields have not been completed, the operator saves time in programming the infusion pump and is further prevented from entering extraneous information that may impact the operation of the infusion pump.

In sample configurations, an infusion pump includes a tube, a pump motor configured to pump a liquid through the tube, a user interface, a memory, a controller coupled to the memory and the pump motor, and pump programming instructions in the memory. The controller executes the pump programming instructions to configure the infusion pump to present a multi-tabbed graphical user interface (GUI) on the user interface to guide an operator through programming of the infusion pump. In sample configurations, each tab of the GUI includes data fields for entry of data for operation of the infusion pump. During programming of the infusion pump, an operator selection of a tab of the GUI for data entry and data entries for a selected tab of the GUI are received. Once all required data entries for the selected tab of the GUI have been entered, a next tab indicator is presented on or adjacent a next tab of the GUI to direct the operator to select the next tab for the entry of additional input data. In sample configurations, the selected tab may include at least one optional data field. In such a case, the controller may execute additional instructions to present the next tab indicator on or adjacent the next tab of the GUI when all required data entries for the selected tab have been entered but data entry into the at least one optional data field is incomplete. In such a configuration, the controller may further execute instructions to shade the at least one optional data field in the user interface to indicate that data entry for the shaded at least one optional data field is not required for a selected mode of operation of the infusion pump.

In sample configurations, the next tab indicator may comprise an icon such as a triangle pointing to the next tab or text associated with the next tab for operator data input. The controller may further present the tabs of the multi-tabbed GUI from left to right across the user interface whereby the respective tabs of the GUI include data fields for data entry of parameters relating to drug data, patient data, infusion data, and the like. The user interface may include a touchscreen display that displays a keyboard in the user interface when the touchscreen display is touched.

BRIEF DESCRIPTION OF THE DRAWINGS

The drawing figures depict multiple views of one or more implementations, by way of example only, not by way of limitations. In the figures, like reference numerals refer to the same or similar elements. The same numeral is used to represent the same or similar element across the multiple views. If multiple elements of the same or similar type are present, a letter may be used to distinguish between the multiple elements. When the multiple elements are referred to collectively or a non-specific one of the multiple elements is being referenced, the letter designation may be dropped.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings. Moreover, while described with respect to an ambulatory peristaltic infusion pump for pain management, homecare, outpatient infusions, and the like, it will be appreciated by those skilled in the art that the multi-tabbed graphical user interface (GUI) described herein may be used with a variety of other pump types that require multiple steps to program the pumps.

Figure 1:
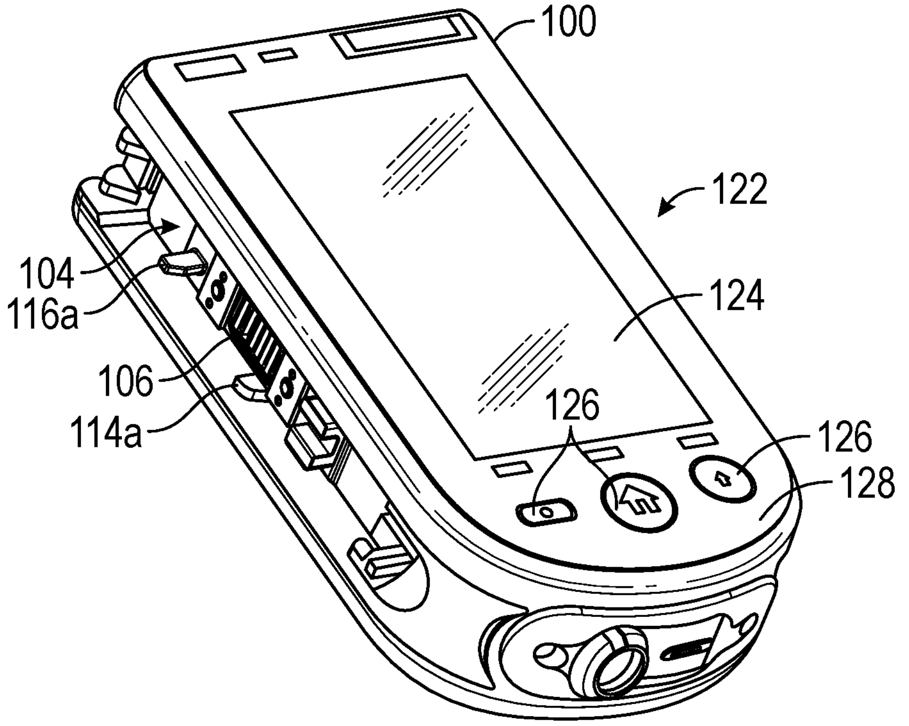
FIG. 1 is a perspective view of an example ambulatory peristaltic infusion pump.
Figure 2:
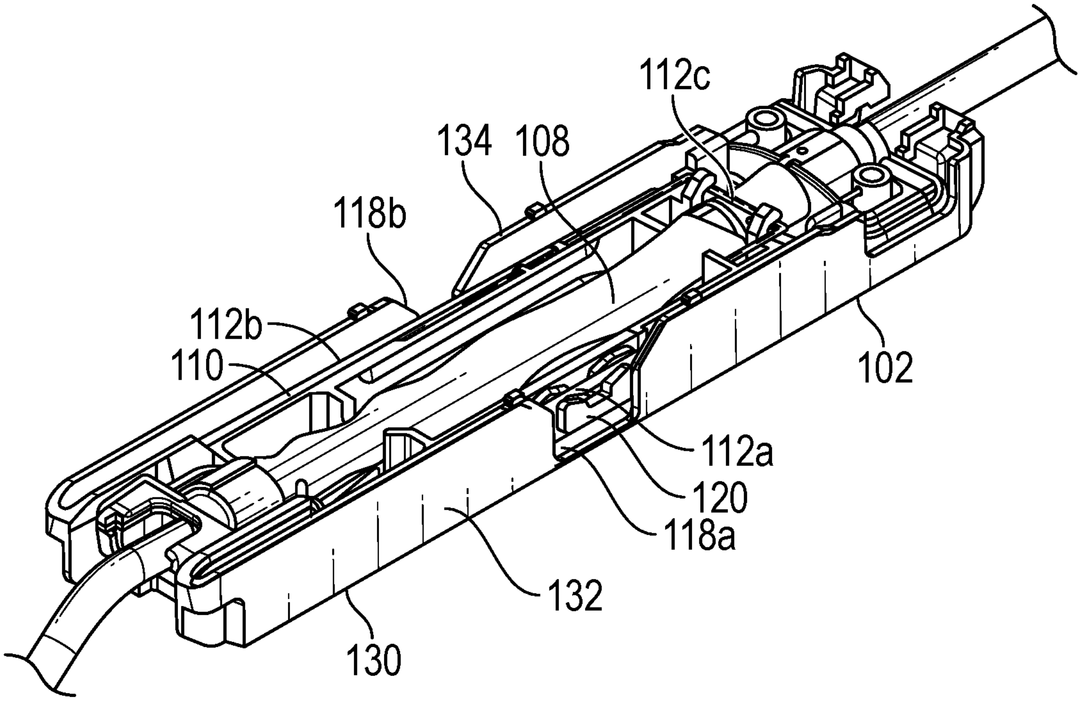
FIG. 2 is a perspective view of an example cassette with a free flow prevention clamp for use with the ambulatory peristaltic infusion pump of FIG. 1.

FIG. 1 depicts an example ambulatory peristaltic infusion pump 100, while FIG. 2 depicts an example cassette 102 for use with the ambulatory peristaltic infusion pump 100. The ambulatory peristaltic infusion pump 100 includes a receptacle 104 configured to receive the cassette 102. A peristaltic pump 106 within the receptacle 104 acts upon a tube 108 extending through a channel within the cassette 102 to pump fluid from a fluid container (e.g., a bag or a bottle; not shown) into a patient. An example free flow prevention clamp 110 is positioned within the cassette 102 to allow fluid flow through the tube 108 when the cassette 102 is coupled to the ambulatory peristaltic infusion pump 100 within the receptacle 104 (during which time the peristaltic pump 106 controls fluid flow through the tube 108) and to selectively cut off fluid flow through the tube 108 when the cassette 102 is not coupled to the ambulatory peristaltic infusion pump 100 in order to prevent unintentional fluid flow through the tube 108 (e.g., free flow).

The ambulatory peristaltic infusion pump 100 includes a user interface 122 for interacting with the ambulatory peristaltic infusion pump 100. The illustrated user interface 122 includes a display 124 (which may be a touchscreen) and buttons 126. A user controls operation of the ambulatory peristaltic infusion pump 100 via the user interface 122. The ambulatory peristaltic infusion pump 100 additionally includes a housing 128 for containing and supporting the components of the ambulatory peristaltic infusion pump 100 such as the peristaltic pump 106, electronics, power supplies, and the like.

The free flow prevention clamp 110 includes a first elongate section 112*a*, a second elongate section 112*b*, and a clamping section 112*c*. The housing 130 of the cassette 102 supports the free flow prevention clamp 110. The clamping section 112*c* is positioned within the cassette geometry such that, when the cassette 102 is received within the receptacle 104 of the ambulatory peristaltic infusion pump 100, the clamping section 112*c* extends across the channel receiving the tube 108. The housing 130 of the cassette 102 may be rigid plastic or other material capable of supporting the tube 108 and free flow prevention clamp 110.

The ambulatory peristaltic infusion pump 100 also includes a pair of arc cams 114*a* and 114*b*. First arc cam 114*a* is shown on one side of the receptacle illustrated in FIG. 1, but the second arc cam 114*b* is hidden from view. The pair of arc cams 114*a* and 114*b* engage the elongate sections 112*a*, 112*b* of the free flow prevention clamp 110 in order to lift the clamping section 112*c*. Additionally, the ambulatory pump 100 includes a pair of wedge cams 116*a* and 116*b*. A first wedge cam 116*a* is shown on one side of the receptacle 104 illustrated in FIG. 1, but the second wedge cam 116*b* is hidden from view. The pair of wedge cams 116*a* and 116*b* transition the free flow prevention clamp 110 from an open, manufactured/shipped state to an operational state, which is described in further detail below.

The cassette 102 also includes a first cutout 118*a* in a sidewall 132 of the cassette 102 and a second cutout 118*b* in an opposite sidewall 134 of the cassette 102. Additionally, the cassette 102 includes a touch pad 120 positioned on the first elongate section 112*a* adjacent a mid-point of the first elongate section 112*a* and the first cutout 118*a*. The touch pad 120 and cutout 118*a* together facilitate engagement of the first elongate section 112*a* by a finger of an operator in order to manually lift the clamping section 112*c* to allow fluid flow through the tube 108 (e.g., for priming the cassette 102) when the cassette 102 is not received within the receptacle 104 of the ambulatory peristaltic infusion pump 100. The touch pad 120 may be a press fit piece of rigid plastic. Although the touch pad 120 is illustrated as only on the first elongate section 112*a*, the touch pad 120 also may be provided on the second elongate section 112*b*.

Figure 3:
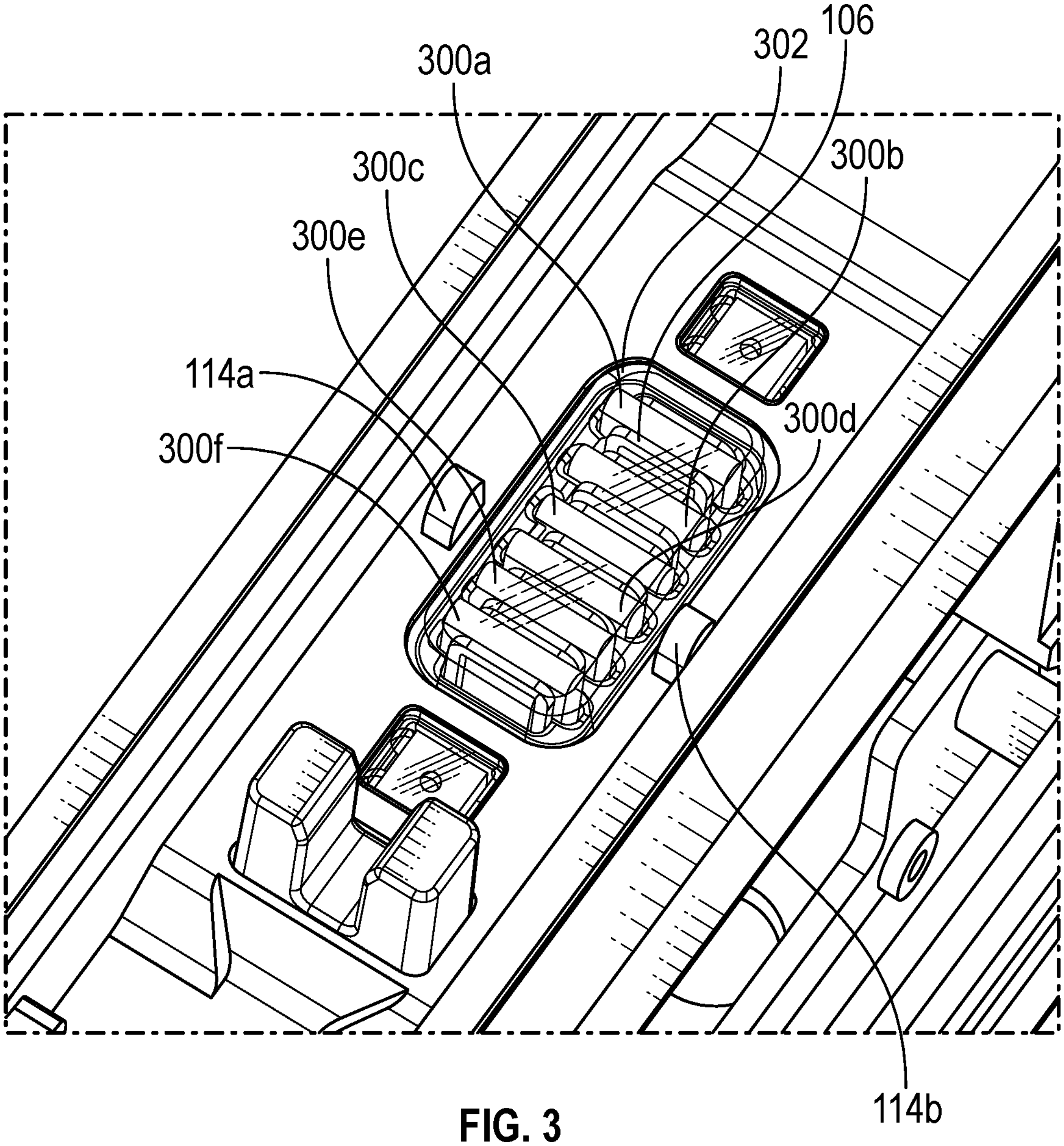
FIG. 3 is a partial perspective view of the ambulatory peristaltic infusion pump of FIG. 1 illustrating cams that engage the free flow prevention clamp when the cassette is coupled to the ambulatory peristaltic infusion pump.

FIG. 3 depicts the arc cams 114*a* and 114*b* and peristaltic pump 106 of the ambulatory peristaltic infusion pump 100. The peristaltic pump 106 includes multiple pump fingers 300 (six pump fingers 300*a-f* illustrated in FIG. 3). A flexible barrier 302 separates the pump fingers 300 (and other pump components of a pumping mechanism) from the receptacle 104 receiving the cassette 102 with the tube 108. The flexible barrier 302 provides a barrier between the fluid delivery apparatus/cassette and the pumping mechanism to prevent fluid from damaging components of the pumping mechanism.

Figure 4:
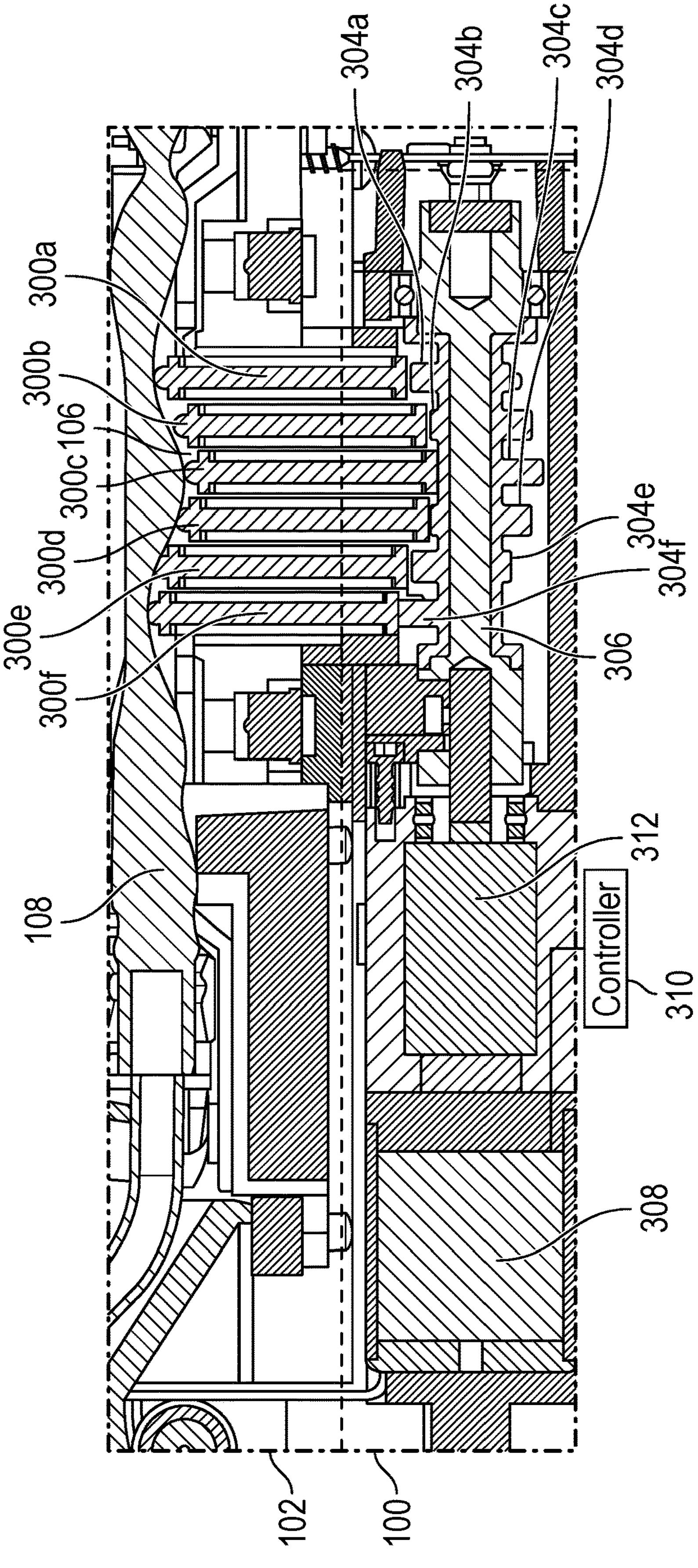
FIGS. 4 and 5 are cutaway views of the ambulatory peristaltic infusion pump of FIG. 1 illustrating pump fingers and cams for moving the pump fingers.
Figure 5:
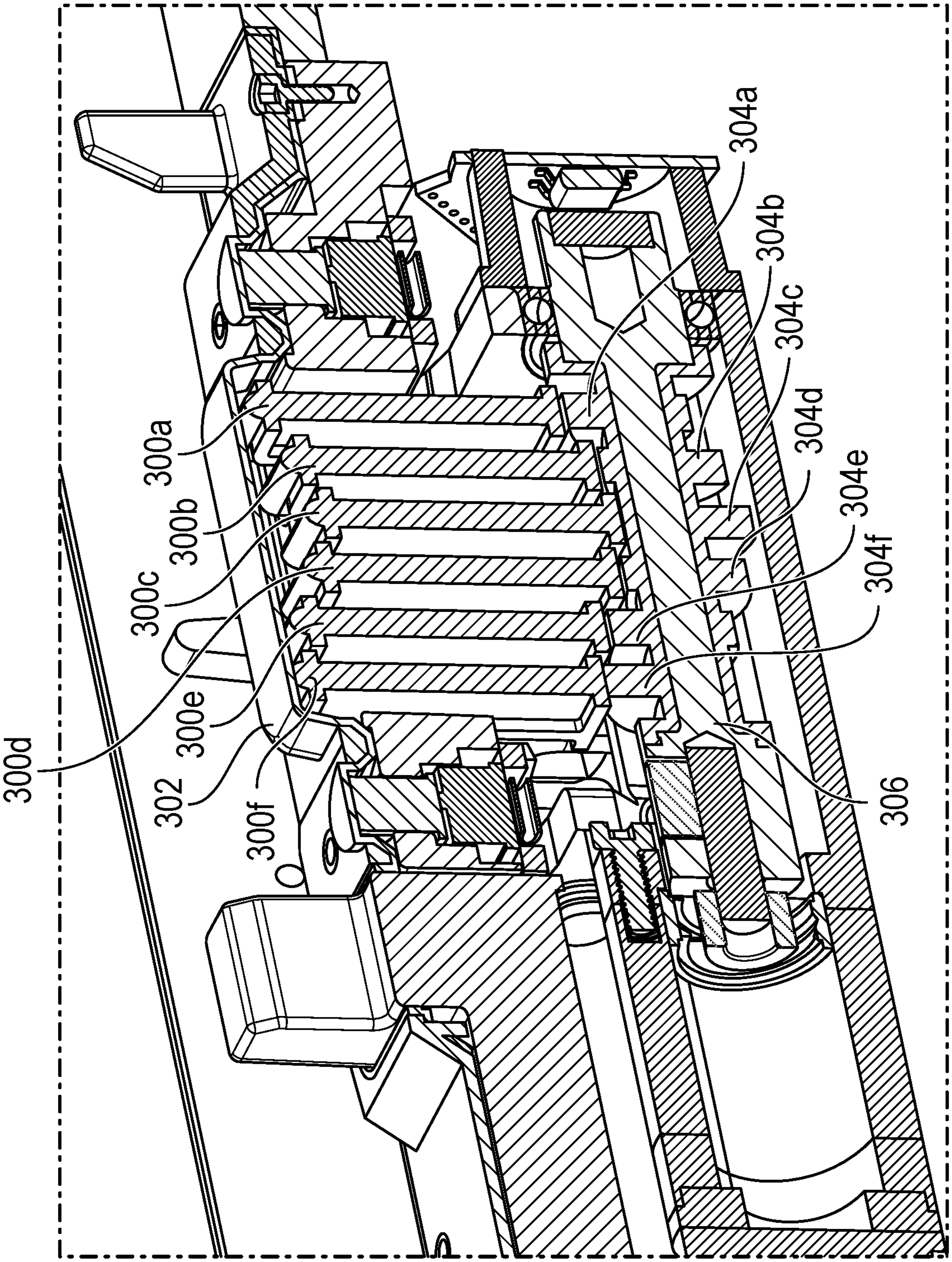

FIGS. 4 and 5 are cutaway views of the ambulatory peristaltic infusion pump 100 with the cassette 102 inserted into the receptacle 104 of the ambulatory peristaltic infusion pump 100. Multiple cams 304 (six cams 304*a-f*) supported by a cam shaft 306 act on respective pump fingers 300*a*-300*f*. The cams 304*a*-304*f* respectively raise and lower the pump fingers 300*a*-300*f*, which engage the tube 108 of the cassette 102 in order to force fluid though the tube 108. A pump motor 308 under control of a controller 310 turns the cam shaft 306 by way of a gearbox 312. As the cam shaft 306 turns, the cams 304*a*-300*f*, which are offset from each other in an axial direction, raise and lower respective pump fingers 300*a*-300*f*. For example, cam 304*a* raises and lowers pump finger 300*a*; cam 304*b* raises and lowers pump finger 300*b*, and the like. As described below with respect to FIGS.

8 and 9, the controller 310 may be a standalone or embedded processor configured to carry out instructions in order to control operations of the ambulatory peristaltic infusion pump 100.

The controller 310 may include a main controller such as a dual core 32 bit processor from NXP of Eindhoven, Netherlands (e.g., model #MCIMX7S5EVM08SC), a microcontroller from NXP (e.g., model #MKV11Z128VLF7), a pump motor driver from ST Microelectronics of Geneva, Switzerland (e.g., model #STSPIN250), and a magnetic encoder from Austria microsystems of Premstaetten, Austria (e.g., model number AS5601-ASOM). The microcontroller receives pump cam shaft revolutions per minute (RPM) corresponding to the infusion rate from a System Control Core of the main processor. The microcontroller develops a pulse width modulation (PWM) motor drive parameter relating to the desired cam shaft RPM. The PWM output of the microcontroller becomes the motor drive input to the pump motor driver, which contains motor drive transistors and protection circuitry. The rotation of the cam shaft 306 of the pumping mechanism is measured by the magnetic encoder. At specified time intervals, the output of the encoder is read by the microcontroller, which uses the encoder value to compute the speed of the cam shaft 306 and the position of the pump rotation. These values are then used to modify the PWM output to maintain the correct cam shaft RPM.

Prior to operation, the operator of the ambulatory peristaltic infusion pump 100 of FIGS. 1-5 is requested to enter a number of parameters to program the ambulatory peristaltic infusion pump 100. During the programming of the ambulatory peristaltic infusion pump 100 to deliver an infusion to a patient, the operator of the ambulatory peristaltic infusion pump 100 may be required to enter many different types of parameters (e.g., patient information, drug information, infusion parameters, etc.). For example, when the ambulatory peristaltic infusion pump 100 is used to infuse one or more drugs into a patient, the ambulatory peristaltic infusion pump 100 may be programmed to specify the drug(s) to be infused, patient data, and infusion (flow rate) data.

Figure 6:
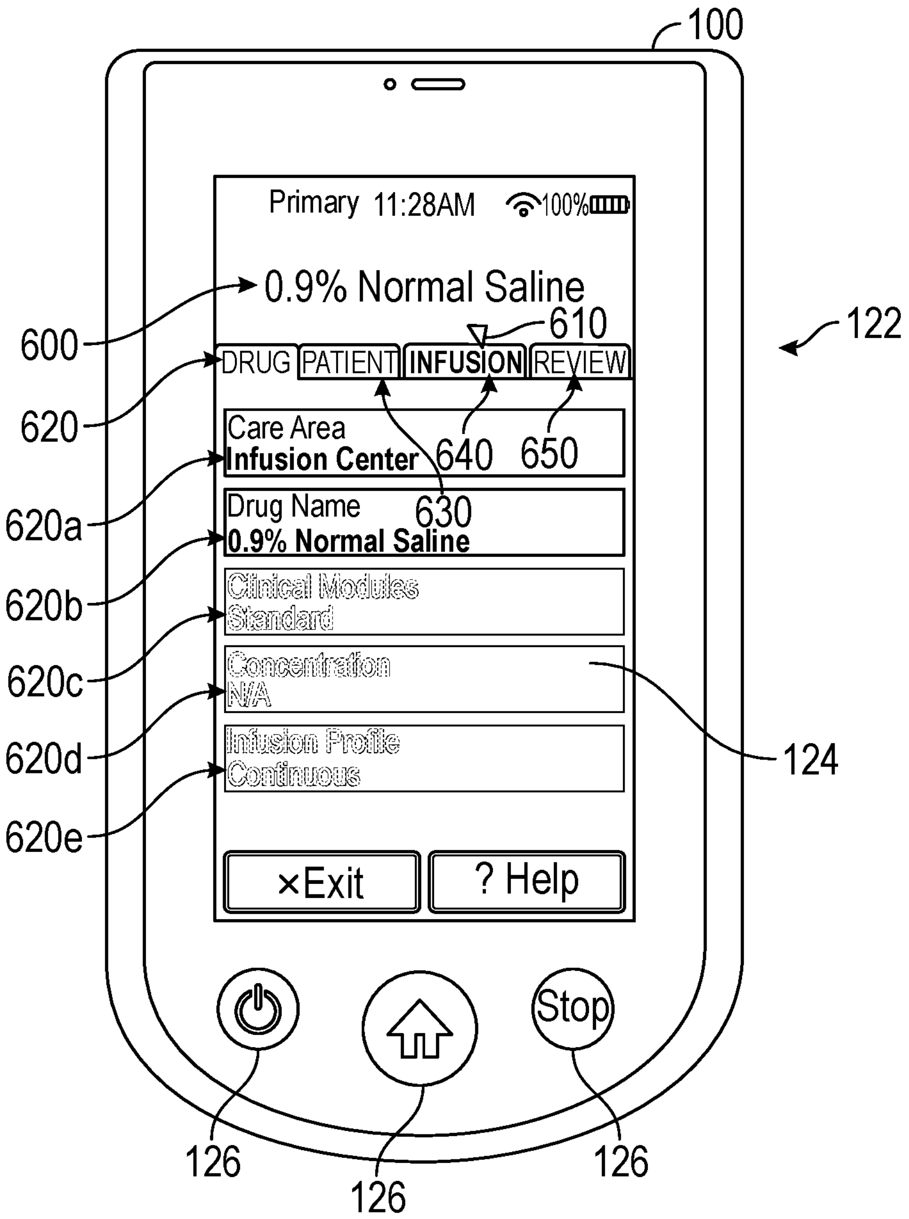
FIG. 6 illustrates a sample multi-tabbed graphical user interface (GUI) including a next tab indicator in a sample configuration.

As illustrated in FIG. 6, the user interface 122 of the ambulatory peristaltic infusion pump 100 may include a multi-tabbed GUI 600 including a next tab indicator 610 that directs the operator in the entry of the parameters in a sample configuration. Due to the small form factor of the ambulatory peristaltic infusion pump 100, the maximum size of the display (and associated display area) is limited. Accordingly, in a sample configuration is it desired for the next tab indicator 610 to be a small icon, such as a small triangle, which is placed on or adjacent the next tab to identify the next tab or text associated with the next tab for operator data input.

As illustrated, a number of tabs are presented from left to right across the user interface 122. A first tab 620 provides data entry boxes 620*a*-620*e* for entry of data specifying the care area (620*a*), drug name (620*b*), clinical modifier (620*c*), drug concentration (620*d*), infusion profile (620*e*), and the like. It will be appreciated that not all data entry boxes are required for particular drugs or modes of operation. In this example, data entry boxes 620*c*-620*e* are shaded to indicate that the information in data entry boxes 620*c*-620*e* is optional and not required for the selected drugs or current mode of operation.

Second tab 630 provides data entry boxes (not shown) for entry of patient data, and third tab 640 similarly provides data entry boxes (not shown) for entry of infusion data relating to the desired flow rate, time of day for infusion, and the like. A fourth tab 650 provides a summary of the inputted parameters for operator review prior to operation of the ambulatory peristaltic infusion pump 100. Additional, different tabs may be provided in other modes of operation. It will be appreciated that the user interface 122 may include a touchscreen display 124 that pulls up a keyboard (e.g., an AZERTY, QWERTY, QWERTZ, or QZERTY keyboard) when touched. Alternatively, a button (not shown) may be used to call up the keyboard for data entry.

The multi-tabbed GUI 600 thus includes multiple tabs (e.g., 620-650) that correspond to categories of parameters for entry (e.g., drug information, patient information, infusion information) and that are presented in progressive order. The operator is required to fill in all required parameters of a particular category before moving on to the next category.

As the operator may be a new user that is untrained or inadequately trained, the operator may not appreciate what parameters are required. Accordingly, the required parameters may be identified by shading the data entry boxes that are optional and not required to be completed before moving on to the next category. In addition, in sample configurations, the operator is further guided in the selection of the next tab by presenting an indicator 610 next to the next tab or text associated with the next tab once all the required parameters under the current tab have been entered. As shown in FIG. 6, the operator may be guided to the next tab 640 to select by placing an indicator 610 such as a small triangle next to the next tab 640 once the required data has been entered for the current tab. In the example of FIG. 6, the indicator 610 informs the operator that the operator may transition directly from tab 620 to tab 640, which is possible once the required data has been entered in tab 620 and provided that all required patient data has already been entered in tab 630. In sample configurations, the "next tab" indicator 610 may be a transient graphic that pulses, fades, or otherwise turns on and off to further attract operator attention. However, it is also possible that the "next tab" indicator 610 is static and does not transition.

Figure 7:
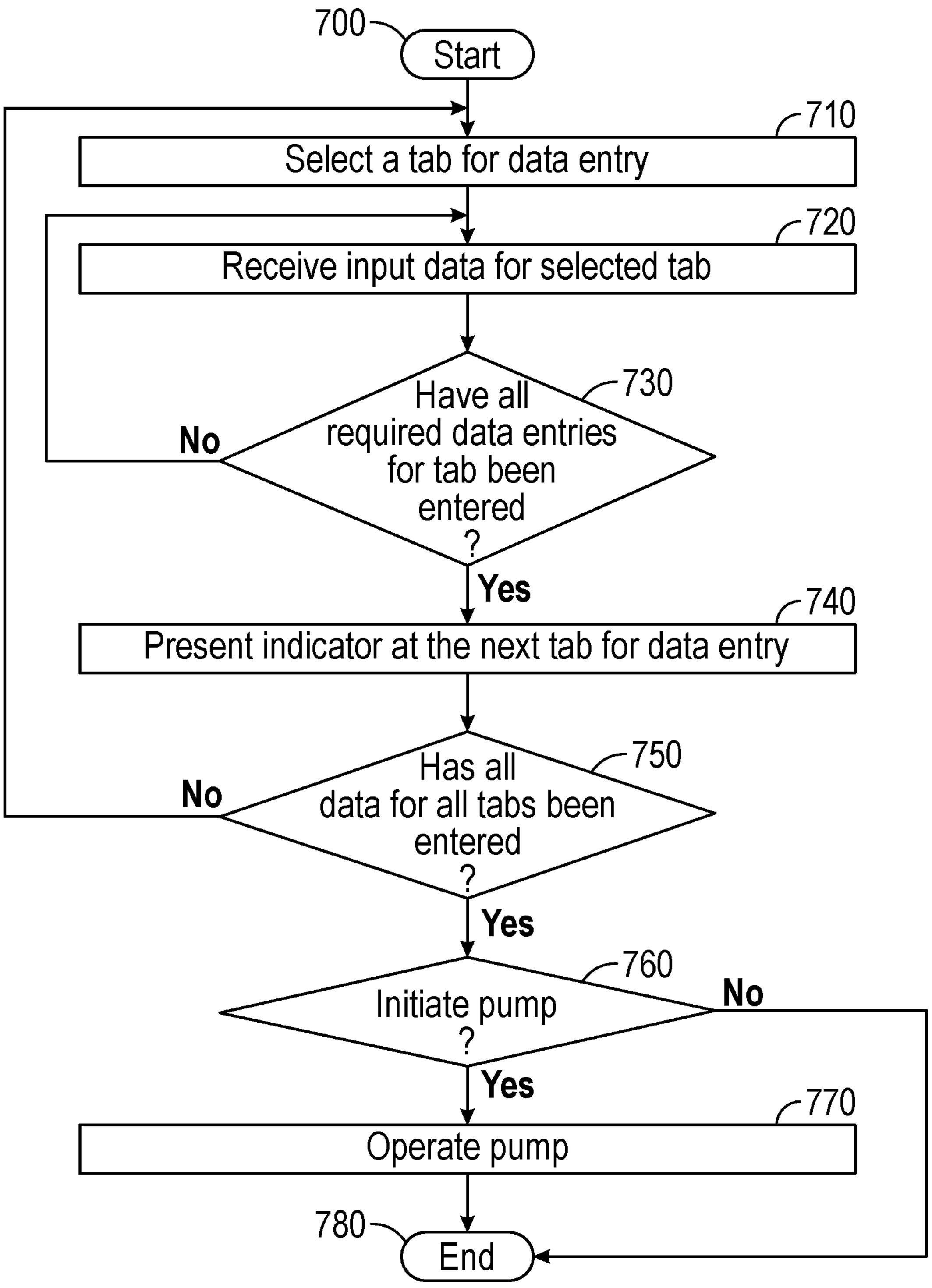
FIG. 7 is a flow chart illustrating the operation of a multi-tabbed GUI of the ambulatory peristaltic infusion pump of FIG. 1 in which the multi-tabbed GUI guides the operator to the next tab using a next tab indicator in a sample configuration.

FIG. 7 is a flow chart illustrating the programming of the ambulatory peristaltic infusion pump 100 using a multi-tabbed GUI 600 that guides the operator to the next tab using a next tab indicator 610 in a sample configuration. As noted above, the multi-tabbed GUI 600 is adapted to enable the operator to enter the parameters necessary to configure the ambulatory peristaltic infusion pump 100 to deliver an infusion to a patient. In the example of FIG. 6, the multi-tabbed GUI 600 includes tabs 620-650 that correspond to categories of parameters for entry (e.g., patient information, drug information, infusion information). The tabs 620-650 are presented in order, with the first parameters to be entered accessed by selecting the tab 620 on the far left. As the information is completed, the operator selects the respective tabs 620-650 (moving from left to right) until all required parameters are completed.

Controller 310 of the ambulatory peristaltic infusion pump 100 may be programmed to implement the process of FIG. 7. As illustrated in FIG. 7, the process starts at 700. The operator may select one of the tabs 620-650 for data entry at 710, typically starting with the left-most tab. However, the user may start at 720 without selecting one of the tabs 620-650. The required data for that tab is input by the operator at 720 using, for example, a keyboard that pops up upon selection of the tab either via a button selection via a button 126 or by a touch selection via a touchscreen 124. The operator is required to fill in all required parameters of a particular category under a tab 620-650 before moving on to the next category. Due to the number of items present under the selected tab, it may not be readily apparent to the operator when all required parameters have been entered under the selected tab and that the operator may move on to the next tab 620-650. Accordingly, a determination is made at 730 whether all required data entries for the selected tab have been entered. After the requisite entries have been made, the operator may repeat data entry at 730 and may change previously entered parameters. It will be appreciated that the required data entries may be less than all of the data entries represented by the displayed data entry boxes as some parameters may be optional.

In sample configurations, the data entry starts with the left most tab 620, and the elections made at tab 620 drive the choices offered to the user in at tabs 630, 640, and ultimately 650. Depending on the selection of the drug within tab 620, tab 630 (patient data) is toggled on or off accordingly as not all drugs bear requirements to refine patient data. Additionally, the choices made at tabs 620 and 630 determine what parameters are to be entered at tab 640. Then, the results of the data entry are summarized at tab 650. In sample configurations, the software forces a left to right order of data entry.

In the sample configurations, the tabs are precisely organized to move the operator from one tab to the next, with the entries from one tab influencing what is delivered and expected in the next tab. The next tab indicator 610 appears simultaneously with the next tab even becoming activated and thus selectable by the user. In other words, the operator must get through all required entries of the first tab 620 before being given access to the next tab (either tab 630 or tab 640 pending elections at tab 620) and then the next tab (640) and then the final tab 650 for review of the selections. An operator may return to a prior tab, but the operator may not skip ahead as the tabs are greyed-out and unselectable until enabled for completion.

Once it has been determined that all required data entries for a current tab have been entered at 730, the indicator 610 is presented at the next tab or text associated with the next tab at 740 to guide the operator in the data entry. In addition, the next tab indicator 610 being presented, this is also the first time that the next tab is selectable. Prior to a determination that all required data entries have been entered for the current tab at 730, the next tab is greyed out and unselectable. At 750, a determination is made whether all required data for all tabs has been entered. If not, the process returns to 710 to select the next tab for data entry. It is noted that only one new tab is made available for data entry and that an operator may return to a previous tab. Once all required data for all tabs has been entered, the entered data is confirmed at review tab 650 before giving the operator the option at 760 to initiate operation of the ambulatory peristaltic infusion pump 100. If the user selects to initiate the ambulatory peristaltic infusion pump 100, the ambulatory peristaltic infusion pump 100 is operated at 770. Otherwise, the process ends at 780.

Figure 8:
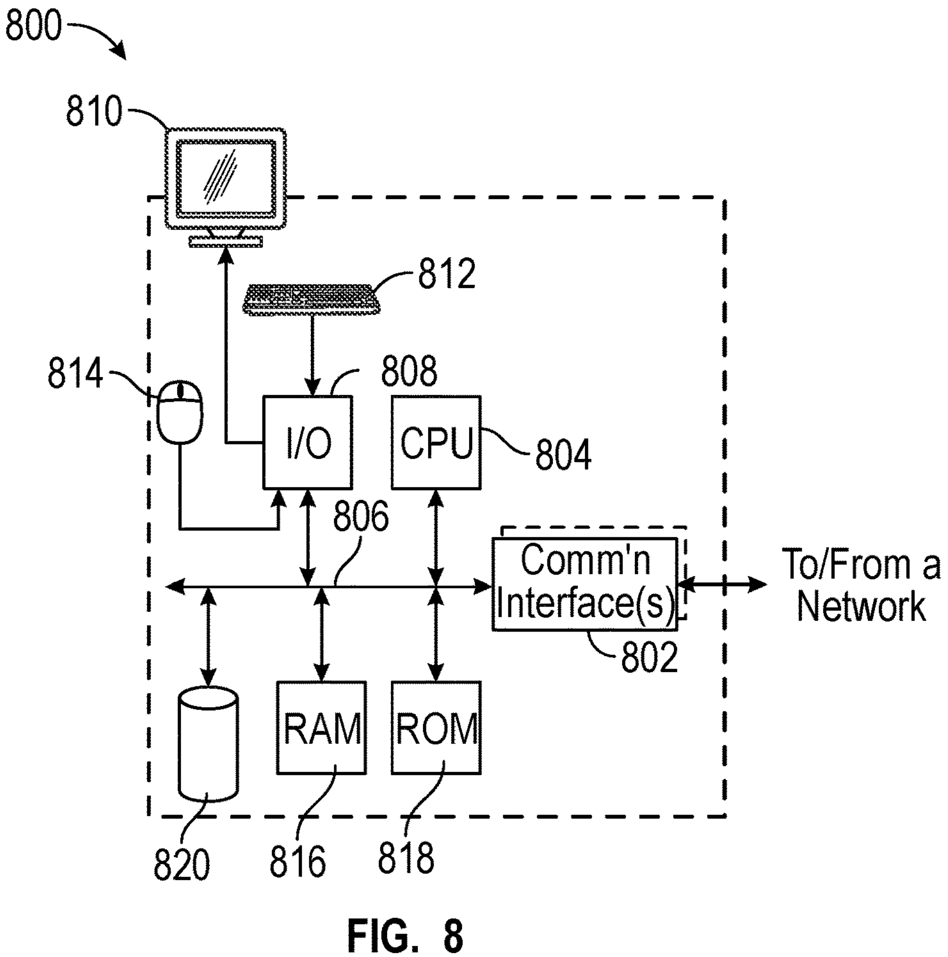
FIG. 8 is a functional block diagram illustrating a general-purpose computer hardware platform configured to implement the functional examples described with respect to FIGS. 6-7.
Figure 9:
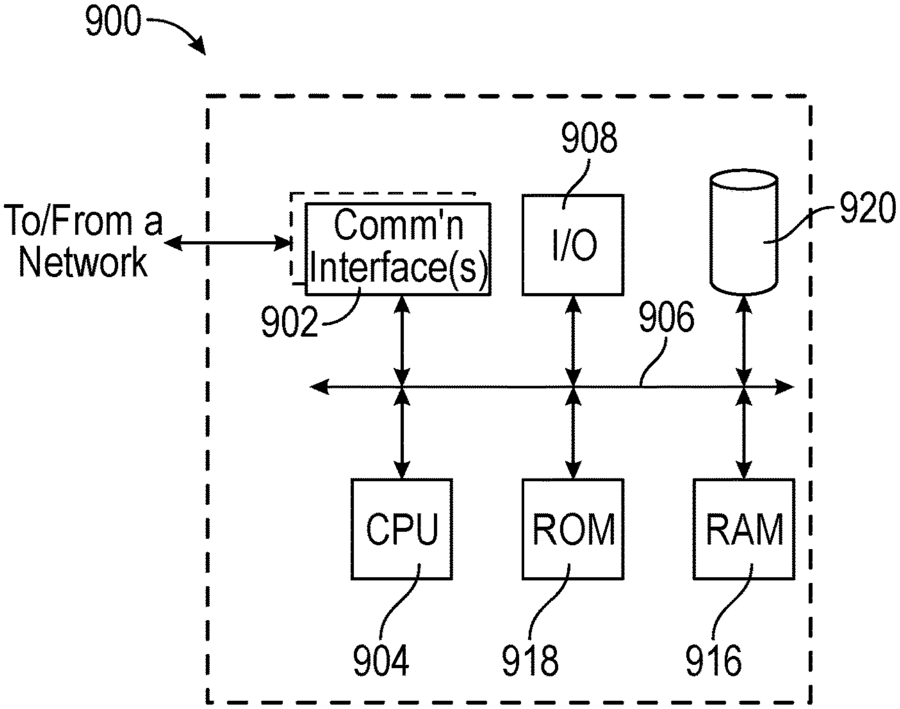
FIG. 9 is another functional block diagram illustrating a general-purpose computer hardware platform configured to implement the functional examples described with respect to FIGS. 6-7.

FIGS. 8 and 9 are functional block diagrams illustrating general-purpose computer hardware platforms configured to implement the functional examples described with respect to FIGS. 1-7 as discussed above.

Specifically, FIG. 8 illustrates an example computer platform 800 and FIG. 9 depicts an example computer 900 with user interface elements, as may be used to implement in a personal computer, controller 310 of the ambulatory peristaltic infusion pump 100, or other type of workstation or terminal device. It is believed that those skilled in the art are familiar with the structure, programming, and general operation of such computer equipment and as a result the drawings should be self-explanatory.

Hardware of an example server computer 800 (FIG. 8) includes a data communication interface 802 for packet data communication. The server computer 800 also includes a central processing unit (CPU) 804, in the form of circuitry forming one or more processors, for executing program instructions. The server platform hardware typically includes an internal communication bus 806, program and/or data storage in Random Access Memory (RAM) 816, Read Only Memory ROM) 818, and a mass storage (e.g., disk storage) device 820 for storing various programs and data files to be processed and/or communicated by the server computer 800, although the server computer 800 often receives programming and data via network communications via data communication interface 802. In one example, as shown in FIG. 8, the computer system 800 further includes a video display unit 810, (e.g., a liquid crystal display (LCD) or a cathode ray tube (CRT)), an alphanumeric input device 812 (e.g., a keyboard), a cursor control device 814 (e.g., a mouse), each of which communicate via an input/output device (I/O) 808. The hardware elements, operating systems, and programming languages of such server computers 800 are conventional in nature, and it is presumed that those skilled in the art are adequately familiar therewith. Of course, the server functions may be implemented in a distributed fashion on a number of similar hardware platforms, to distribute the processing load.

Hardware of a computer type user terminal device 900, such as a PC or tablet computer, similarly includes a data communication interface 902, CPU 904, main memory including RAM 916 and ROM 918, one or more mass storage (e.g., disk) devices 920 for storing user data and the various executable programs, an internal communication bus 906, and an input/output device (I/O) 908 (see FIG. 9).

Aspects of the methods for pump control, as outlined above, may be embodied in programming in general purpose computer hardware platforms (such as described above with respect to FIGS. 8 and 9), e.g., in the form of software, firmware, or microcode executable by a networked computer system such as a server or gateway, and/or a programmable nodal device. Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software, from one computer or processor into another, for example, from a processor 804 of the system 800 and/or from a controller 310 of a pump 100 to a computer or software of another system (not shown). Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to one or more of "non-transitory," "tangible" or "storage" media, terms such as computer or machine "readable medium" refer to any medium that participates in providing instructions to a processor for execution.

Hence, a machine-readable medium may take many forms, including but not limited to, a tangible storage medium or physical transmission medium. Non-transitory storage media include, for example, optical or magnetic disks, such as any of the storage devices in any computer(s) or the like. The non-transitory storage media may also include storage media such as dynamic memory, for example, the main memory of a machine or computer platform. Tangible transmission media include coaxial cables, copper wire, and fiber optics, including the wires that include a bus within a computer system. Carrier-wave transmission media can take the form of electric or electromagnetic signals, or acoustic or light waves such as those generated during radio frequency (RF) and light-based data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, cables or links transporting a carrier wave, or any other medium from which a computer can read programming code and/or data. Many of these forms of computer readable media may be involved in carrying one or more sequences of one or more instructions to a processor for execution.

Program instructions for implementing the process described herein may include a software or firmware implementation encoded in any desired language. Programming instructions, when embodied in machine readable medium accessible to a processor of a computer system or device, render the computer system or device into a special-purpose machine that is customized to perform the operations specified in the program performed by the controller 310 of the pump 100.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is ordinary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 105 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that includes a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that includes the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing describes what is considered to be the best mode and other examples, it is understood that various modifications may be made and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. An infusion pump, comprising:

a tube;

a pump motor configured to pump a liquid through the tube;

a user interface;

a memory;

a controller coupled to the memory and the pump motor; and pump programming instructions in the memory, wherein the controller is configured to receive the pump programming instructions from the memory and to execute the received pump programming instructions, wherein execution of the pump programming instructions by the controller configures the infusion pump to:

present a multi-tabbed graphical user interface (GUI) on the user interface to guide an operator through programming of the infusion pump, each tab of the GUI including data fields for entry of data for operation of the infusion pump;

receive an operator selection of a tab of the GUI for data entry;

receive data entries for a selected tab of the GUI; and once all required data entries for the selected tab of the GUI have been entered, present on or adjacent a second tab of the GUI an indicator that directs the operator to select the second tab for the entry of additional input data and activate the second tab of the GUI for selection.

2. The infusion pump of claim 1, wherein the selected tab includes at least one optional data field and wherein the controller executes additional instructions to present the indicator on or adjacent the second tab of the GUI when all required data entries for the selected tab have been entered but data entry into the at least one optional data field is incomplete.

3. The infusion pump of claim 2, wherein the controller executes instructions to shade the at least one optional data field in the user interface to indicate that data entry for the shaded at least one optional data field is not required for a selected mode of operation of the infusion pump.

4. The infusion pump of claim 1, wherein the indicator comprises a transient graphic that identifies the second tab for operator data input.

5. The infusion pump of claim 4, wherein the transient graphic is a triangle that points to the second tab or text associated with the second tab to draw the operator's attention to the second tab or the text associated with the second tab.

6. The infusion pump of claim 1, wherein the controller executes instructions to present tabs of the multi-tabbed GUI from left to right across the user interface and to make tabs after an initial tab selectable by the operator once all required data entries for a previous tab of the GUI have been entered.

7. The infusion pump of claim 6, wherein the respective tabs of the GUI include data fields for data entry of parameters relating to drug data, patient data, and infusion data.

8. The infusion pump of claim 1, wherein the user interface comprises a touchscreen display that displays a keyboard in the user interface when the touchscreen display is touched.

9. A method of programming an infusion pump, comprising:

presenting a multi-tabbed graphical user interface (GUI) on a user interface of the infusion pump to guide an operator through programming of the infusion pump, each tab of the GUI including data fields for entry of data for operation of the infusion pump;

receiving an operator selection of a tab of the GUI for data entry;

receiving input data for the selected tab of the GUI; and once all required data entries for the selected tab of the GUI have been entered, presenting on or adjacent a second tab of the GUI an indicator that directs the operator to select the second tab for the entry of additional input data and activating the second tab of the GUI for selection.

10. The method of claim 9, wherein the selected tab includes at least one optional data field, and wherein presenting the indicator comprises presenting the indicator on or adjacent the second tab of the GUI when all required data entries for the selected tab have been entered but data entry into the at least one optional data field is incomplete.

11. The method of claim 10, further comprising shading the at least one optional data field in the user interface to indicate that data entry for the shaded at least one optional data field is not required for a selected mode of operation of the infusion pump.

12. The method of claim 9, wherein presenting the indicator comprises presenting a transient graphic that identifies the second tab for operator data input.

13. The method of claim 12, wherein presenting the indicator comprises presenting a triangle that points to the second tab or text associated with the second tab to draw the operator's attention to the second tab or the text associated with the second tab.

14. The method of claim 9, wherein presenting the multi-tabbed GUI to the user interface comprises presenting tabs of the multi-tabbed GUI from left to right across the user interface and making tabs after an initial tab selectable by the operator once all required data entries for a previous tab of the GUI have been entered.

15. The method of claim 14, wherein presenting the multi-tabbed GUI to the user interface comprises presenting respective tabs including data fields for data entry of parameters relating to drug data, patient data, and infusion data.

16. The method of claim 9, further comprising displaying a keyboard in the user interface when a touchscreen display of the user interface is touched.

17. The method of claim 9, further comprising initiating operation of the infusion pump when all required data for all tabs has been entered.

18. A non-transitory controller-readable storage medium storing controller-executable instructions for programming an infusion pump that, when executed by a controller of the infusion pump cause the infusion pump to perform operations comprising:

presenting a multi-tabbed graphical user interface (GUI) on a user interface of the infusion pump to guide an operator through programming of the infusion pump, each tab of the GUI including data fields for entry of data for operation of the infusion pump;

receiving an operator selection of a tab of the GUI for data entry;

receiving input data for the selected tab of the GUI; and once all required data entries for the selected tab of the GUI have been entered, presenting on or adjacent a second tab of the GUI an indicator that directs the operator to select the second tab for the entry of additional input data and activating the second tab of the GUI for selection.

19. The medium of claim 18, wherein the selected tab includes at least one optional data field, further comprising instructions stored on the medium that when executed by the controller cause the infusion pump to perform operations comprising presenting the indicator on or adjacent the second tab of the GUI when all required data entries for the selected tab have been entered but data entry into the at least one optional data field is incomplete.

20. The medium of claim 19, further comprising instructions stored on the medium that when executed by the controller cause the infusion pump to perform operations comprising shading the at least one optional data field in the user interface to indicate that data entry for the shaded at least one optional data field is not required for a selected mode of operation of the infusion pump.

* * * * *